US011447439B2

(12) United States Patent
Janssen et al.

(10) Patent No.: US 11,447,439 B2
(45) Date of Patent: Sep. 20, 2022

(54) METHOD FOR INHIBITING UNWANTED RADICAL POLYMERISATION OF ACRYLIC ACID PRESENT IN A LIQUID PHASE P

(71) Applicant: BASF SE, Ludwigshafen am Rhein (DE)

(72) Inventors: Nicole Janssen, Ludwigshafen am Rhein (DE); Peter Zurowski, Ludwigshafen am Rhein (DE); Ulrich Hammon, Ludwigshafen am Rhein (DE); Sylke Haremza, Ludwigshafen am Rhein (DE)

(73) Assignee: BASF SE

( * ) Notice: Subject to any disclaimer, the term of this patent is extended or adjusted under 35 U.S.C. 154(b) by 0 days.

(21) Appl. No.: 17/263,415

(22) PCT Filed: Jul. 16, 2019

(86) PCT No.: PCT/EP2019/069079
§ 371 (c)(1),
(2) Date: Jan. 26, 2021

(87) PCT Pub. No.: WO2020/020697
PCT Pub. Date: Jan. 30, 2020

(65) Prior Publication Data
US 2021/0309598 A1    Oct. 7, 2021

(30) Foreign Application Priority Data
Jul. 26, 2018 (EP) .................................. 18185760

(51) Int. Cl.
*C07C 51/50* (2006.01)
*C07C 51/44* (2006.01)

(52) U.S. Cl.
CPC .............. *C07C 51/50* (2013.01); *C07C 51/44* (2013.01)

(58) Field of Classification Search
CPC .......... C07C 51/50; C07C 57/04; C07C 51/44
See application file for complete search history.

(56) References Cited

U.S. PATENT DOCUMENTS

| 3,493,471 | A | * | 2/1970 | Bashaw ................ C08F 20/62 |
|   |   |   |   | 203/92 |
| 4,110,370 | A | | 8/1978 | Engelbach et al. |
| 4,317,926 | A | | 3/1982 | Sato et al. |
| 5,198,578 | A | | 3/1993 | Etzkorn et al. |
| 5,780,679 | A | | 7/1998 | Egly et al. |
| 5,831,124 | A | | 11/1998 | Machhammer et al. |
| 5,856,562 | A | | 1/1999 | Mine et al. |
| 6,207,022 | B1 | | 3/2001 | Dockner et al. |
| 6,441,228 | B2 | | 8/2002 | Nakahara et al. |
| 6,888,025 | B2 | | 5/2005 | Hirao et al. |
| 6,966,973 | B2 | | 11/2005 | Nakahara et al. |
| 7,109,372 | B2 | | 9/2006 | Hirao et al. |
| 7,319,167 | B2 | | 1/2008 | Nakahara et al. |
| 7,332,624 | B2 | | 2/2008 | Nishimura et al. |
| 9,212,122 | B2 | | 12/2015 | Blum et al. |
| 2004/0242826 | A1 | | 12/2004 | Nishimura |
| 2011/0036704 | A1 | * | 2/2011 | Blum .................... C07C 51/252 |
|   |   |   |   | 203/31 |

FOREIGN PATENT DOCUMENTS

| DE | 1905013 A1 | 9/1969 |
| DE | 2449780 A1 | 4/1976 |
| DE | 3521458 A1 | 12/1985 |
| DE | 4308087 A1 | 9/1994 |
| DE | 4335172 A1 | 4/1995 |
| DE | 4436243 A1 | 4/1996 |
| DE | 19606877 A1 | 8/1997 |
| DE | 19627847 A1 | 1/1998 |
| DE | 19627850 A1 | 1/1998 |
| DE | 19734171 A1 | 2/1999 |
| DE | 19835247 A1 | 2/1999 |
| DE | 19740252 A1 | 3/1999 |
| DE | 19740253 A1 | 3/1999 |
| DE | 19810962 A1 | 9/1999 |
| DE | 19837520 A1 | 2/2000 |
| DE | 69701590 T2 | 9/2000 |
| DE | 19924532 A1 | 11/2000 |
| DE | 19924533 A1 | 11/2000 |
| DE | 10028582 A1 | 12/2001 |
| DE | 10115277 A1 | 6/2002 |
| DE | 10131297 A1 | 1/2003 |

(Continued)

OTHER PUBLICATIONS

European Search Report for EP Patent Application No. 18185760.8, dated Jan. 24, 2019, 3 pages.
Holger Becker, "Polymerisationsinhibierung von (Meth-)Acrylaten", Technische Universität Darmstadt Universitäts- und Landesbibliothek, TU Darmstadt, Fachbereich Chemie, 2003, 234 pages.
International Preliminary Reporton Patentability received for PCT Patent Application No. PCT/EP2019/069079, dated Feb. 4, 2021, 12 pages (6 pages of English Translation and 6 pages of Original Document).
International Search Report and Written Opinion received for PCT Patent Application No. PCT/EP2019/069079, dated Aug. 7, 2019, 14 pages (6 pages of English Translation and 8 pages of Original Document).

*Primary Examiner* — Yevgeny Valenrod
*Assistant Examiner* — Blaine G Doletski
(74) *Attorney, Agent, or Firm* — Faegre Drinker Biddle & Reath LLP

(57) ABSTRACT

Process for inhibiting the undesired free-radical polymerization of acrylic acid present in a liquid phase P, wherein the acrylic acid content of P is at least 10% by weight, the liquid phase P comprises in the range from 25 to 1000 ppmw of glyoxal based on the weight of the acrylic acid present in P and the liquid phase P is admixed with furfural in an amount that results in a furfural content in the range from 25 to 1000 ppmw based on the weight of the acrylic acid present in P. Liquid phase P, wherein the acrylic acid content of P is at least 10% by weight and the liquid phase P comprises in the range from 25 to 1000 ppmw of glyoxal and in the range from 25 to 1000 ppmw of furfural in each case based on the weight of the acrylic acid present in P.

12 Claims, No Drawings

(56) References Cited

FOREIGN PATENT DOCUMENTS

| | | | |
|---|---|---|---|
| DE | 10235847 A1 | 8/2003 | |
| DE | 10223058 A1 | 12/2003 | |
| DE | 10336386 A1 | 3/2004 | |
| DE | 10243625 A1 | 4/2004 | |
| DE | 10245585 A1 | 4/2004 | |
| DE | 10246119 A1 | 4/2004 | |
| DE | 10247240 A1 | 4/2004 | |
| DE | 10332758 A1 | 5/2004 | |
| DE | 102005052917 A1 | 10/2007 | |
| DE | 102007029053 A1 | 1/2008 | |
| DE | 102007004960 A1 | 7/2008 | |
| DE | 102008040799 A1 | 12/2008 | |
| DE | 102009027401 A1 * | 2/2010 | ........... C07C 51/445 |
| DE | 102009027401 A1 | 2/2010 | |
| DE | 102008041573 A1 | 3/2010 | |
| DE | 102010042216 A1 | 6/2011 | |
| EP | 0117146 A1 | 8/1984 | |
| EP | 0253409 A2 | 1/1988 | |
| EP | 0608838 A2 | 8/1994 | |
| EP | 0695736 A1 | 2/1996 | |
| EP | 0722926 A1 | 7/1996 | |
| EP | 0765856 A1 | 4/1997 | |
| EP | 0770592 A1 | 5/1997 | |
| EP | 0778255 A1 | 6/1997 | |
| EP | 0792867 A2 | 9/1997 | |
| EP | 0854129 A1 | 7/1998 | |
| EP | 0920408 A1 | 6/1999 | |
| EP | 0982287 A1 | 3/2000 | |
| EP | 0982288 A2 | 3/2000 | |
| EP | 0982289 A2 | 3/2000 | |
| EP | 1015410 A1 | 7/2000 | |
| EP | 1015411 A1 | 7/2000 | |
| EP | 1041062 A2 | 10/2000 | |
| EP | 1066239 A1 | 1/2001 | |
| EP | 1066240 A1 | 1/2001 | |
| EP | 1068174 A1 | 1/2001 | |
| EP | 1110940 A2 | 6/2001 | |
| EP | 1298120 A1 | 4/2003 | |
| EP | 1388532 A1 | 2/2004 | |
| EP | 1388533 A1 | 2/2004 | |
| EP | 1396484 A1 | 3/2004 | |
| EP | 1484303 A2 | 12/2004 | |
| EP | 1484308 A1 | 12/2004 | |
| EP | 1484309 A1 | 12/2004 | |
| EP | 1710227 A1 | 10/2006 | |
| GB | 1258491 A | 12/1971 | |
| GB | 2160543 A | 12/1985 | |
| JP | 11-035519 A | 2/1999 | |
| JP | 2001-348359 A | 12/2001 | |
| WO | 98/01414 A1 | 1/1998 | |
| WO | 98/01415 A1 | 1/1998 | |
| WO | 99/14181 A1 | 3/1999 | |
| WO | 99/14182 A1 | 3/1999 | |
| WO | 99/50219 A1 | 10/1999 | |
| WO | 99/50220 A1 | 10/1999 | |
| WO | 99/50222 A1 | 10/1999 | |
| WO | 00/53560 A1 | 9/2000 | |
| WO | 00/53561 A1 | 9/2000 | |
| WO | 00/76370 A1 | 12/2000 | |
| WO | 01/92190 A1 | 12/2001 | |
| WO | 01/96270 A2 | 12/2001 | |
| WO | 01/96271 A2 | 12/2001 | |
| WO | 02/09839 A1 | 2/2002 | |
| WO | 02/55469 A1 | 7/2002 | |
| WO | 03/11804 A2 | 2/2003 | |
| WO | 03/41832 A1 | 5/2003 | |
| WO | 03/78378 A1 | 9/2003 | |
| WO | 2004/018089 A1 | 3/2004 | |
| WO | 2004/035514 A1 | 4/2004 | |
| WO | 2004/063138 A1 | 7/2004 | |
| WO | 2005/035478 A2 | 4/2005 | |
| WO | 2005/042459 A1 | 5/2005 | |
| WO | 2005/047224 A1 | 5/2005 | |
| WO | 2005/047226 A1 | 5/2005 | |
| WO | 2005/073160 A1 | 8/2005 | |
| WO | 2006/002713 A1 | 1/2006 | |
| WO | 2006/092272 A2 | 9/2006 | |
| WO | 2006/114506 A1 | 11/2006 | |
| WO | 2006/136336 A2 | 12/2006 | |
| WO | 2007/074044 A1 | 7/2007 | |
| WO | 2007/074045 A1 | 7/2007 | |
| WO | 2007/090991 A2 | 8/2007 | |
| WO | 2008/090190 A1 | 7/2008 | |
| WO | 2010/012586 A1 | 2/2010 | |
| WO | 2011/000808 A2 | 1/2011 | |
| WO | 2012/045738 A1 | 4/2012 | |

\* cited by examiner

METHOD FOR INHIBITING UNWANTED RADICAL POLYMERISATION OF ACRYLIC ACID PRESENT IN A LIQUID PHASE P

CROSS-REFERENCE TO RELATED APPLICATIONS

This application is a national stage application (under 35 U.S.C. § 371) of PCT/EP2019/069079, filed Jul. 16, 2019, which claims benefit of European Application No. 18185760.8, filed Jul. 26, 2018, both of which are incorporated herein by reference in their entirety.

The present invention relates to a process for inhibiting undesired free-radical polymerization of acrylic acid present in a liquid phase P and to the liquid phase produced during performance of the process.

Acrylic acid is an important monomer which is used as such, in the form of its salts and/or in the form of its esters (for example alkyl ester) for producing polymers that are used for example as adhesives or as materials superabsorbent toward water (cf. for example WO 02/055469 A and WO 03/078378 A).

Production of acrylic acid may be carried out, for example, by heterogeneously catalyzed partial oxidation of a $C_3$-precursor compound (for example propylene, propane, acrolein, propionaldehyde, propionic acid, propanol and/or glycerol) in the gas phase (cf. for example WO 2010/012586 A.

U.S. Pat. No. 5,198,578 A, EP 1 710 227 A, EP 1 015 410 A, EP 1 484303 A, EP 1 484 308 A, EP 1 484 309 A, US 2004/0242826 A, WO 2006/136336 A, DE 10 028 582 A and WO 2007/074044 A).

Such a heterogeneously catalyzed partial gas phase oxidation generally does not afford pure acrylic acid but rather merely an acrylic acid-comprising product gas mixture which comprises not only acrylic acid but also constituents distinct from acrylic acid from which the acrylic acid must be separated.

Both the type and the quantitative fraction of the constituents distinct from acrylic acid in the product gas mixture can be influenced inter alia through the choice of the $C_3$-precursor compound, through the employed catalyst, through the reaction conditions at which the heterogeneously catalyzed partial gas phase oxidation is performed, through the type and amount of the impurity constituents distinct from the $C_3$-precursor compound that are present in the $C_3$-precursor compound employed as a raw material and through the choice of the diluent gases that generally dilute the reactants in the reaction gas mixture (cf. for example DE 10 131 297 A, DE 10 2005 0529 17 A, WO 2007/074044 A and DE 10 028 582 A).

Separation of the acrylic acid from the product gas mixture of the heterogeneously catalyzed partial gas phase oxidation of a $C_3$-precursor compound typically employs a combination of different separation processes in order in the most economic fashion possible to achieve a purity of the acrylic acid which is appropriate to the subsequent intended use thereof. The combination employed in a particular case thus depends inter alia on the type and amount of the constituents distinct from acrylic acid that are present in the product gas mixture.

A feature that is common to essentially all possible combinations of separation processes for separating acrylic acid from the product gas mixture of a heterogeneously catalyzed partial gas phase oxidation of a $C_3$-precursor compound is that optionally after direct and/or indirect cooling of the aforementioned product gas mixture, acrylic acid present in the product gas mixture is brought into the condensed, especially liquid, phase in a main separation step.

This may be effected for example by absorption into a suitable solvent (for example water, high-boiling organic solvents, aqueous solutions) and/or by partial or substantially complete condensation (for example fractionating condensation) (cf. in this regard for example the specifications EP 1 388 533 A, EP 1 388 532 A, DE 10 235 847 A, EP 792 867 A, WO 98/01415 A, U.S. Pat. No. 7,332,624 B2, U.S. Pat. No. 6,888,025 B2, U.S. Pat. No. 7,109,372 B2, EP 1 015 411 A, EP 1 015 410 A, WO 99/50219 A, WO 00/53560 A, WO 02/09839 A, DE 10 235 847 A, WO 03/041832 A, DE 10 223 058 A, DE 10 243 625 A, DE 10 336 386 A, EP 854 129 A, U.S. Pat. No. 7,319,167 B2, U.S. Pat. No. 4,317,926 A, DE 1 983 752 0 A, DE 1 960 687 7 A, DE 1 905 013 25 A, DE 10 247 240 A, DE 1 974 025 3 A, EP 695 736 A, EP 982 287 A, EP 1 041 062 A, EP 117 146 A, DE 4 308 087 A, DE 4 335 172 A, DE 4 436 243 A, DE 19 924 532 A, DE 10 332 758 A and DE 19 924 533 A). Acrylic acid separation may also be undertaken as in EP 982 287 A, EP 982 289 A, DE 10 336 386 A, DE 10 115 277 A, DE 19 606 877 A, DE 19 740 252 A, DE 19 627 847 A, EP 920 408 A, EP 10 681 74 A, EP 10 662 39 A, EP 10 662 40 A, WO 00/53560 A, WO 00/53561 A, DE 10 053 086 A and EP 982 288 A. Advantageous modes of separation also include the processes described in the specifications WO 2004/063138 A, WO 2008/090190 A, WO 2004/035514 A, DE 10 243 625 A and DE 10 235 847 A.

Constituents distinct from acrylic acid that are present in the product gas mixture of the heterogeneously catalyzed partial gas phase oxidation are normally also brought into the condensed phase with the acrylic acid.

The specifications DE 10 2009 0274 01 A, DE 10 2008 041 573 A, DE 10 2008 040 799 A, EP 1 298 120 A and EP 1 396 484 A disclose that when the reaction mixture from the heterogeneously catalyzed partial gas phase oxidation of the $C_3$-precursor compound to acrylic acid comprises $C_2$-impurities, for example ethylene, in the context of the heterogeneously catalyzed partial gas phase oxidation, elevated amounts of the aldehyde (monomeric) glyoxal as a byproduct generally occur in the product gas mixture and that (monomeric) glyoxal is typically brought into the condensed phase with the acrylic acid in appreciable proportions in the above-described main separation of the acrylic acid from the product gas mixture.

When the reaction gas mixtures from the heterogeneously catalyzed partial gas phase oxidation of the $C_3$-precursor compound (for example propylene) comprise both the abovementioned $C_3$-impurities and $C_2$-impurities the described main separation of the acrylic acid from the product gas mixture from the heterogeneously catalyzed partial gas phase oxidation normally generates a condensed phase comprising not only acrylic acid but also propionic acid and glyoxal.

It is known from EP 770592 A that even the smallest amounts of aldehydic impurities present in acrylic acid such as for example glyoxal can significantly impair the properties of the acrylic acid. EP 770 592 A thus teaches that the individual aldehyde proportions in an acrylic acid should be below 1 ppm in order to obtain optimal product qualities in the context of the use of such an acrylic acid especially in free-radical polymerization reactions for production of superabsorbent polymers for example or of polymers effective as dispersants for oil drilling mud or as flocculants.

The separation steps to be employed in order to separate the acrylic acid in the desired purity from a liquid phase obtained in the course of the described main separation and comprising the target product acrylic acid and the undesired byproducts glyoxal and propionic acid may be a very wide range of combinations of for example adsorptive, extractive, desorptive, distillative, stripping, rectificative, azeotropically distillative, azeotropically rectificative and crystallizative processes depending on the objectives and the type and amount of other additionally present undesired secondary components.

Liquid phases comprising the target product acrylic acid and the undesired byproducts glyoxal and propionic acid may be obtained in a very wide variety of types and with different quantitative fractions in the course of the abovementioned separation process, which liquid phases require intermediate storage and/or subjection to thermal stress by heating for example.

This is disadvantageous since both long residence times and thermal stress increase the probability of undesired free-radical polymerization of the acrylic acid present in the liquid phase.

The latter applies all the more since the physical similarity of acrylic acid and some secondary components necessitates the use of elevated residence times in the separating apparatus when using noncrystallizative thermal separation processes to achieve an appreciable separating effect and monomeric glyoxal promotes the tendency of acrylic acid to undergo undesired free-radical polymerization to a significantly greater extent than other possible impurities (cf. DE 102008041573 A, DE 102008040799 A and DE 102009027401 A).

It is well known that addition of inhibitors to acrylic acid present in the liquid phase can counter the polymerization-promoting influence of residence time and thermal stress (cf. for example "Polymerisationsinhibierung von (Meth-)Acrylaten" [Inhibition of polymerization of (meth)acrylates], thesis of Dipl.-Ing. Holger Becker, Technische Universität Darmstadt, 2003).

The variety of inhibitors recommended in the prior art in this regard is great (cf. for example EP 765 856 A and DE 69 701 590 T2 which acknowledge a small fraction of these inhibitors) and also comprises for example compounds of the element copper (cf. for example JP 2001348359 A).

However, according to EP 1 396 484 A (especially lines 16 and 17 of column 2) none of the known inhibitors systems is capable of satisfactory results. Furthermore, the diversity of the inhibitors recommended in the prior art according to EP 1 396 484 A (for example column 7, paragraph [0024] and column 1, lines 40 to 44) comprises no appreciable preference.

In particular, EP 1 396 484 A notes in column 3, lines 5 to 10 that while the known inhibitors are able to relatively effectively inhibit the undesired free-radical polymerization of acrylic acid due to thermal stress thereon, the inhibiting action in particular of said inhibitors in respect of causation and/or promotion of undesired free-radical polymerization of acrylic acid by impurities present therein such as glyoxal is insufficient.

One way of overcoming the described difficulties is to avoid the formation of undesired byproducts such as propionic acid and glyoxal in the heterogeneously catalyzed partial gas phase oxidation of $C_3$-precursor compounds (these are precursor compounds having three carbon atoms) of acrylic acid to afford acrylic acid (for example through appropriate catalyst selection (cf. for example JP 11-35519 A) or through use of high-purity $C_3$-precursor raw materials (thus producing for example reaction gas mixtures comprising neither $C_2$-impurities nor n-propane nor cyclopropane;

DE 3521458 A describes for example the possibility of purifying propylene produced from n-propane and the specifications WO 2004/018089 A and WO 01/92190 A describe for example producing propylene from methanol (an altered raw material basis)). However this is disadvantageous since the expenditure required in this regard impairs the economy of acrylic acid production.

WO 2012/045738 A (BASF SE), corresponding to U.S. Pat. No. 9,212,122 B2, describes a process for inhibiting the undesired free-radical polymerization of acrylic acid present in a liquid phase P whose acrylic acid content is at least 10% by weight and which, based on the weight of the acrylic acid present therein, additionally comprises at least 100 ppmw of propionic acid and at least 100 ppmw of glyoxal, wherein the liquid phase P is admixed with at least one chemical compound of the element copper.

EP 1 110 940 A2 (Nippon Shokubai) relates to a process for purifying acrylic acid in which a weight ratio of furfural: acrolein of ≤100 is established in the distillation of acrylic acid.

It is an object of the present invention to provide an improved process for inhibiting the undesired free-radical polymerization of acrylic acid present in a liquid phase P. The process should in particular be technically simple to perform and economic and should not adversely affect product quality, i.e. acrylic acid quality.

The inventors have accordingly found a process for inhibiting the undesired free-radical polymerization of acrylic acid present in a liquid phase P, wherein the acrylic acid content of P is at least 10% by weight, the liquid phase P comprises in the range from 25 to 1000 ppmw of glyoxal based on the weight of the acrylic acid present in P and the liquid phase P is admixed with furfural in an amount that results in a furfural content in the range from 25 to 1000 ppmw based on the weight of the acrylic acid present in P.

The inventors have further found a liquid phase P, wherein the acrylic acid content of P is at least 10% by weight and the liquid phase P comprises in the range from 25 to 1000 ppmw of glyoxal and in the range from 25 to 1000 ppmw of furfural in each case based on the weight of the acrylic acid present in P.

The process has the particular feature that the liquid phase P comprises in the range from 50 to 500 ppmw of glyoxal based on the weight of the acrylic acid present in P and the liquid phase P is admixed with furfural in an amount that results in a furfural content in the range from 50 to 500 ppmw based on the weight of the acrylic acid present in P.

The process according to the invention is based on the experimental finding, which is surprising compared to the current knowledge of the prior art, that glyoxal in the presence of furfural no longer promotes, but rather retards, the undesired free-radical polymerization of acrylic acid. Furfural=2-furaldehyde=furan-2-carboxaldehyde, CAS no. 98-01-1.

By reaction with for example secondary constituents comprising hydroxyl groups (for example $H_2O$, alcohols such as ethanol etc.) monomeric glyoxal

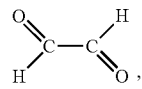

is capable of forming hemiacetals and/or acetals. Such hemiacetals and/or acetals generally no longer exhibit the polymerization-promoting effect typical for monomeric glyoxal or in any case exhibit it only to an extent that is substantially reduced in comparison therewith.

However in the case of hemiacetals/acetals of glyoxal the formation reaction is often a readily reversible reaction, which is why, under the influence of elevated temperature or upon removal of glyoxal from the corresponding equilibrium, these hemiacetals/acetals reform monomeric glyoxal which then has a corresponding influence on the undesired free-radical polymerization.

In the case of water as the secondary constituent comprising hydroxyl groups, the following readily reversible acetal formation reactions are known (in this case reference may also be made to hydrates of glyoxal):

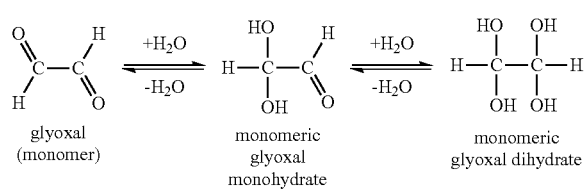

glyoxal (monomer)   monomeric glyoxal monohydrate   monomeric glyoxal dihydrate

Both abovementioned glyoxal hydrates are formed even under relatively mild conditions (low temperatures, limited water contents are sufficient).

The terms "monomeric" glyoxal monohydrate and "monomeric" glyoxal dihydrate are used here to distinguish from "polyglyoxal" and "oligoglyoxal" hydrates.

Shown hereinbelow by way of example are diglyoxal hydrates and triglyoxal hydrates:

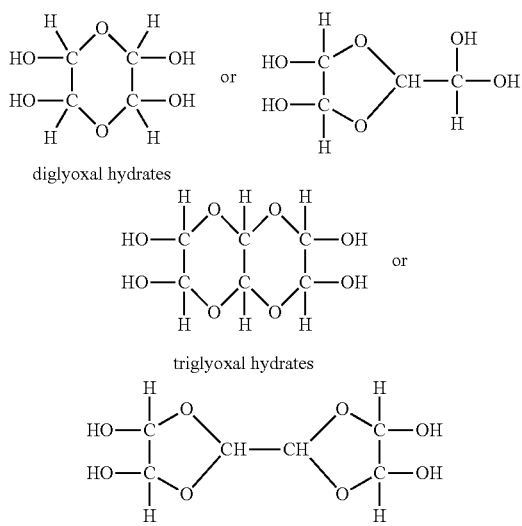

diglyoxal hydrates triglyoxal hydrates

It is thought that the formation of the polyglyoxal hydrates proceeds via the monomeric glyoxal dihydrate as an intermediate (cf. also DE-A 102008041573, DE-A 102008040799 and DE-A 102009027401).

In contrast to the formation of the monomeric glyoxal hydrates, the formation of the polyglyoxal hydrates requires elevated temperatures (formation thereof generally only occurs to an appreciable extent at temperatures above 50° C.) and/or longer reaction times.

For the reasons stated above the term "glyoxal" is therefore in the present document to be understood as subsuming not only monomeric glyoxal but also glyoxal that is reversibly chemically bound in the form of acetals and/or hemiacetals of monomeric glyoxal for example (unless explicitly stated otherwise and unless the term "glyoxal" explicitly includes at least one additional characterization such as for example "monomeric" glyoxal or "di"glyoxal "hydrate" or "monomeric" glyoxal "monohydrate").

The general term "glyoxal" is thus in the present document always to be understood as meaning the total amount of monomeric glyoxal and reversibly bound glyoxal.

Contents of glyoxal reported in "% by weight" and "ppmw" are thus in the present document always to be understood as meaning the total amount present of monomeric glyoxal and reversibly bound glyoxal, such as for example in monomeric glyoxal monohydrate and in monomeric glyoxal dihydrate, but are always calculated as "monomeric glyoxal" (i.e. they refer to the weight fraction of the altogether present amount of $H_2C_2O_2$ units).

This is particularly relevant to the process mode according to the invention since water is normally the main byproduct of a heterogeneously catalyzed partial gas phase oxidation of a $C_3$-precursor compound of acrylic acid to afford acrylic acid. Furthermore, due to its relatively high molar heat capacity for example, steam is often co-used as a diluent gas in the reaction gas mixture for heterogeneously catalyzed partial gas phase oxidations of $C_3$-precursor compounds to afford acrylic acid (cf. for example EP 253 409 A). The main separation of acrylic acid from the product gas mixture of a heterogeneously catalyzed partial gas phase oxidation of a $C_3$-precursor compound to afford acrylic acid thus often has liquid phases passed through it which comprise not only acrylic acid, propionic acid and glyoxal but also water. However, glyoxal hydrates may in principle also be formed even in the product gas mixture of the heterogeneously catalyzed partial gas phase oxidation of the $C_3$-precursor compound of acrylic acid.

Furthermore, the prior art often also recommends water or aqueous solutions as absorbents for an absorptive main separation from the product gas mixture of the gas phase partial oxidation of the $C_3$-precursor compound (cf. for example EP-A 1 298 120 and U.S. Pat. No. 7,332,624 B2).

In the context of the present invention the content of glyoxal in a liquid phase P to be treated according to the invention (or in another liquid phase) (i.e. the total content in the liquid phase P of monomeric glyoxal and glyoxal reversibly bound in compounds such as monomeric glyoxal monohydrate and monomeric glyoxal dihydrate (for example, monomeric glyoxal is also capable of reversibly forming hemiacetals and/or acetals with alcohols such as ethanol)) is determined as follows.

First, a derivatization solution D is produced. To this end, 2.0 g of a 50% by weight solution of 2,4-dinitrophenylhydrazine (manufacturer: Aldrich, purity: ≥97%) is dissolved at a temperature of 25° C. in 62 ml of 37.0% by weight aqueous hydrochloric acid (manufacturer: Aldrich, purity: 99.999%). The resulting solution is subsequently stirred into 335 g of distilled water (likewise at a temperature of 25° C.). After 1 hour of stirring at 25° C., filtration affords the derivatization solution D as the resulting filtrate.

To determine the content of glyoxal in a liquid phase P, 1 g of the derivatization solution D (this amount can be increased correspondingly if required) is weighed into a screwtop bottle having a capacity of 10 ml. A sample of the liquid phase P is then weighed into the thus filled screwtop bottle, the amount of sample being in the range from 0.15 to 2.0 g.

The entire contents of the screwtop bottle are then mixed by shaking and then left to stand at a temperature of 25° C. over a period of 10 minutes. During this time the monomeric glyoxal present in the screwtop bottle undergoes chemical reaction with 2,4-dinitrophenylhydrazine to form the corresponding hydrazone H of monomeric glyoxal. However, during this time the 2,4-dinitrophenylhydrazine also removes from the monomeric glyoxal monohydrate and glyoxal dihydrate present in the screwtop bottle the monomeric glyoxal bound therein in the form of the hydrazone H (by contrast, a corresponding removal of monomeric glyoxal from polyglyoxal hydrates present in the screwtop bottle essentially does not occur).

Addition of 0.5 g of glacial acetic acid (manufacturer: Aldrich, purity: ≥99.8%) into the screwtop bottle subsequently freezes the hydrazone formation that has taken place. If the acetic acid addition is accompanied by formation of solid precipitate further acetic acid is successively added to redissolve the precipitate formed (but the total amount of acetic acid added must not exceed 1.0 g). If the precipitate formed has not gone into solution even upon reaching the maximum limit (1.0 g) of the allowed total acetic acid addition 0.5 g of dimethyl phthalate is weighed in. If this addition too is incapable of dissolving the precipitate formed the dimethyl phthalate addition amount is successively increased to bring about this dissolution (but the total amount of dimethyl phthalate added must not exceed 1.0 g). If the precipitate formed has not gone into solution even upon reaching the maximum limit (1.0 g) of the allowed total dimethyl phthalate addition 2 g of a mixture G composed of 9 g of acetonitrile and 1 g of dimethyl phthalate are added. If this addition too is incapable of dissolving the precipitate the addition amount of mixture G is successively increased to bring about this dissolution. The amount of mixture G altogether added to bring about the dissolution of the precipitate normally does not exceed 5 g (all aforementioned dissolution tests are performed at 25° C.).

The solution of the hydrazone H produced in the screwtop bottle as described is subsequently analyzed for its hydrazone content by HPLC (High Pressure Liquid Chromatography) using the following operating conditions (the molar amount thereof directly specifies the molar amount of glyoxal present in the liquid phase P):

Chromatography column to be used: Waters Symmetry C18, 150×4.6 mm, 5 μm (Waters Associates, Milford, Mass., USA);
Injection volume of solution to be analyzed: 50 μl (time t=0);
Temperature: 40° C.
Eluent flow: 1.5 ml/min;
Analysis time: 17 min;
Equilibration time: 8 min;
Eluent: in the period t from >0 min to 15 min, a mixture of 30% by weight of acetonitrile, 50% by weight of water and 20% by weight of tetrahydrofuran (all HPLC grade);
in the period from >15 min to 17 min, a mixture of 65% by weight of acetonitrile, 30% by weight of water and 5% by weight of tetrahydrofuran;
in the period from >17 min to 25 min, a mixture of 30% by weight of acetonitrile, 50% by weight of water and 20% by weight of tetrahydrofuran (the column is then equilibrated and ready to go again for the next analysis).

The retention time of the glyoxal as the hydrazone H is 7.613 min under the the aforementioned conditions.

The analysis is carried out using monochromatic radiation having a wavelength of 365 nm.

The analytical method employed is absorption spectroscopy.

The variation of the eluent over the elution time ensures an elevated separating effect (the liquid phase P generally comprises not only glyoxal but also other by-product aldehydes and/or by-product ketones which form the respective corresponding hydrazone with 2,4-dinitrophenylhydrazine).

Advantageous application-specific calibration of the HPLC method is advantageously carried out using a solution of monomeric glyoxal in methanol which comprises 50 ppmw of monomeric glyoxal (cf. DE-A 10 2008 041 573 and DE-A 10 2008 040 799).

To this end it is treated with the derivatization solution D as described hereinabove and then subjected to the described HPLC analysis.

According to the invention the furfural may be used in pure form or as a solution in a suitable solvent such as acrylic acid, for example. For example the concentration of the furfural in the acrylic acid solvent may be in the range from 0.1% to 10% by weight, in particular 1% to 2% by weight.

In the process according to the invention the liquid phase P will often comprise at least 10% by weight, or at least 20% by weight, in particular at least 30% by weight, or at least 40% by weight, more particularly at least 50% by weight, or at least 60% by weight, or at least 70% by weight, or at least 80% by weight, more particularly at least 90% by weight, or at least 95% by weight, very particularly at least 98% by weight, or at least 99% by weight, of acrylic acid (in each case based on the weight of the liquid phase P).

In the process according to the invention the liquid phase P will often also comprise water. In the process according to the invention the water content of the liquid phase P may in principle be at least 1% by weight, or at least 5% by weight, or at least 10% by weight, or at least 20% by weight, or at least 30% by weight, or at least 40% by weight, or at least 60% by weight, or at least 80% by weight.

However, the process according to the invention is especially also relevant when the liquid phase P to be treated according to the invention comprises less than 30% by weight, for example ≤29% by weight, or ≤27% by weight, or ≤25% by weight, or ≤20% by weight, or ≤15% by weight, or ≤10% by weight, or ≤5% by weight, of water (lower water contents reduce glyoxal hydrate formation). However, the water content of the liquid phase P is often ≥0.1% by weight, or ≥0.5% by weight, or ≥1% by weight (the water content of, for example, glyoxal hydrates is included in the aforementioned reported quantities).

The liquid phase P often comprises high-boiling absorption medium into which the acrylic acid has been absorbed for example from the product gas mixture of the heterogeneously catalyzed partial gas phase oxidation of the $C_3$-precursor compound (cf. for example DE-A 102009027401).

In the present specification high-boiling absorption media are to be understood as meaning absorption media having a boiling point at standard pressure above that of acrylic acid. The boiling point of the absorption medium at standard pressure (1 atm=about $10^5$ Pa) is normally at least 20° C., preferably at least 50° C., particularly preferably at least 75° C. and very particularly preferably at least 100° C. or at least 125° C. above the boiling point of acrylic acid (141° C. at 1 atm; in contrast to the boiling point of propionic acid of 141.35° C. at the same pressure; cf. WO 2007/074045) at the same pressure. The boiling point of the aforementioned absorption medium at standard pressure is often ≤400° C., often ≤350° C. and frequently also ≤300° C. or ≤280° C. It is particularly advantageous when the boiling point of absorption medium is in the range from 200° C. to 350° C. (based on standard pressure). Contemplated absorption media of this kind include for example all of those recommended in the specifications DE-A 10336386, DE-A 02449780, DE-A 19627850, DE-A 19810962, DE-A 04308087, EP-A 0722926 and DE-A 04436243 and also DE-A 102009027401.

The high-boiling absorption media are generally organic liquids. They often consist to an extent of at least 70% by weight of organic molecules comprising no externally active polar groups and are thus for example not capable of forming hydrogen bonds. Particularly advantageous absorption media include for example diphenyl ether, diphenyl (biphenyl), mixtures of diphenyl ether (70% to 75% by weight) and diphenyl (25% to 30% by weight) known as Diphyl®, and also dimethyl phthalate, diethyl phthalate and mixtures of Diphyl and dimethyl phthalate or Diphyl and diethyl phthalate or Diphyl, dimethyl phthalate and diethyl phthalate. One group of mixtures that are very particularly suitable for absorption purposes are those composed of 75% to 99.9% by weight of Diphyl and 0.1% to 25% by weight of dimethyl phthalate and/or diethyl phthalate.

High-boiling absorption media in the context of this specification may also be ionic liquids.

In the process according to the invention the liquid phase P may comprise for example at least 1% by weight, or at least 5% by weight, or at least 10% by weight, or at least 20% by weight, or at least 30% by weight, or at least 40% by weight, or at least 60% by weight, or at least 80% by weight of high-boiling absorption medium.

The process mode according to the invention exhibits its advantageous effect in particular when the liquid phase P comprises in the range from 25 to 1000 ppmw, in particular in the range from 50 to 500 ppmw, of glyoxal based on the weight of the acrylic acid present therein.

In all aforementioned cases the content of propionic acid in the liquid phase P on a corresponding basis (based on the weight of acrylic acid present) may simultaneously be ≥150 ppmw, or ≥200 ppmw, or ≥250 ppmw, or ≥300 ppmw, or ≥350 ppmw, or ≥400 ppmw, or ≥500 ppmw, or ≥600 ppmw, or ≥700 ppmw, or ≥800 ppmw, or ≥1000 ppmw, or ≥1500 ppmw, or ≥2000 ppmw, or ≥2500 ppmw.

In all aforementioned cases the propionic acid content of the liquid phase P on the aforementioned basis is normally ≤5% by weight, frequently ≤4% by weight or ≤3% by weight, often ≤2% by weight, or ≤1% by weight.

It will be appreciated that the liquid phase P may comprise not only glyoxal and propionic acid but also as further secondary components and typical side-reaction products of the heterogeneously catalyzed partial gas phase oxidation of a $C_3$-precursor compound to afford acrylic acid compounds such as formaldehyde, acrolein, crotonaldehyde, benzaldehyde, propionaldehyde, protoanemonine, allyl acrylate, formic acid, acetic acid, maleic acid, benzoic acid and/or maleic anhydride (for example in quantitative fractions as detailed in WO 2006/002713 A, WO 2008/090190 A, DE-A 10 2007 004960 and DE-A 10 2009 027401, especially in the different liquid substance mixtures of the working examples thereof).

As mentioned above it is often necessary for liquid phases P to be treated according to the invention to be stored over a prolonged period. During this period the acrylic acid to a certain extent reacts with itself and by Michael addition forms limited amounts of diacrylic acid (c.f. for example WO 98/01414 A and WO 2005/035478 A).

The process according to the invention is thus also suitable for liquid phases P which, based on the weight of the acrylic acid present in the liquid phase P, comprise not only the abovementioned amounts of glyoxal, propionic acid and acrylic acid but also ≥100 ppmw, or ≥200 ppmw, or ≥300 ppmw, or ≥400 ppmw, or ≥500 ppmw, or ≥600 ppmw, or ≥800 ppmw, or ≥1000 ppmw, or ≥1500 ppmw, or ≥2000 ppmw, or ≥3000 ppmw, or ≥5000 ppmw, or ≥7500 ppmw, or ≥10 000 ppmw, of diacrylic acid.

The content of diacrylic acid in liquid phases P to be treated according to the invention based on the weight of the acrylic acid present therein is generally not more than 20% by weight, often not more than 15% by weight or not more than 10% by weight and frequently not more than 5% by weight.

Diacrylic acid contents of liquid phases P are determinable in simple fashion by high-resolution $^1$H-NMR (cf. "Polymerisationsinhibierung von (Meth-)Acrylaten" [Inhibition of polymerization of (meth)acrylates], thesis of Dipl.-Ing. Holger Becker, Technische Universität Darmstadt, 2003). The method evaluates the specific signal shape and signal position as well as the signal area of the relevant $^1$H resonance lines. The propionic acid contents of liquid phases P are generally determined by gas chromatography. Their acrylic acid contents may likewise be determined by $^1$H-NMR, by gas chromatography or by HPLC.

The process according to the invention is suitable for inhibiting unwanted free-radical polymerization of acrylic acid present in a liquid phase P both during storage thereof and during process-related handling thereof.

The latter case applies especially when the liquid phase P is subjected to a noncrystallizative thermal separation process (the associated temperatures are generally ≥50° C., usually above 60° C. or 70° C., or above 90° C. or 110° C., and preferably ≤150° C.). Said processes are generally thermal separation processes in which in separating columns comprising separating internals gaseous (ascending) and liquid (descending) streams, i.e. two liquid streams, are run in countercurrent and heat and mass transfer takes place as a result of the gradients existing between the streams, thus ultimately bringing about the separating effect desired in the separating column. Examples of such noncrystallizative thermal separation processes are rectification, azeotropic rectification, extraction, desorption, stripping, distillation, azeotropic distillation and adsorption. Since liquid phases P to be treated according to the invention are formed not least when the product gas mixture of the heterogeneously catalyzed partial gas phase oxidation of a $C_3$-precursor compound to afford acrylic acid is subjected to an absorption, or a fractional condensation, or a partial condensation for basic removal of acrylic acid from the product gas mixture, the process according to the invention is also suitable for inhibiting polymerization of liquid phases P occurring in the course of such thermal separation processes. It will be appreciated that the process according to the invention for inhibiting polymerization is also suitable when the liquid phase P is subjected to a crystallizative thermal separation process.

The term "thermal separation process" is intended to express that heat must be supplied to or removed from the system to achieve the desired separating effect (cf. DE-A 10 2008 041573 and DE-A 10 2008 8040799).

The liquid phase P to be treated by processing may comprise the furfural to be added according to the invention as early as from the start of the thermal separation process (i.e. it may be supplied to the thermal process having already been treated in accordance with the invention). However, it will be appreciated that the furfural may also be added only in the course of the thermal separation process (for example in a rectification dissolved in the reflux liquid, or in an absorption dissolved in the absorption medium, or in a fractionating condensation dissolved in the reflux liquid, or in a direct cooling of the product gas mixture of the heterogeneously catalyzed partial gas phase oxidation of the $C_3$-precursor compound dissolved in the quench liquid used for direct cooling).

It will be appreciated that the furfural to be added to the liquid phase P according to the invention need not be the only inhibitor system added to the liquid phase P. On the contrary, the liquid phase P may additionally comprise one or more inhibitors from the group comprising the nitroxyl radicals (also known as N-oxyl radicals) (for example those disclosed in DE-A 19734171 such as 4-hydroxy-2,2,6,6-tetramethyl-piperidine 1-oxyl or 1,4-dihydroxy-2,2,6,6,-tetramethylpiperidine), phenothiazines such as for example dibenzo-1,4-thiazine (phenothiazine), phenolic compounds such as hydroquinone, 2,4-dimethyl-6-t-butylphenol and hydroquinone monomethyl ether, molecular oxygen, cerium salts, for example cerium(III) salts, manganese salts (for example manganese(III) salts such as manganese(III) acetate dihydrate and manganese(III) di-n-butyldithiocarbamate, p-phenylenediamines (for example those disclosed in DE-A 19734171), organic nitroso compounds such as 4-nitrosophenol (and the others disclosed in DE-A 19734171), methylene blue and all other inhibitors disclosed in EP-A 765856 for example. The aforementioned inhibitors may be added to the liquid phase P in appropriate effective amounts, i.e. for example in the range from 5 to 1000 ppmw (based on the weight of the acrylic acid present in P).

When performing noncrystallizative thermal separaton processes on liquid phases P treated in accordance with the invention in separating columns comprising installed separating internals (for example separating trays such as dual-flow trays) it is possible as an additional inhibiting measure to pass air or nitrogen-enriched air (lean air) through the separating column (for example a rectification column or absorption column) as a source of molecular oxygen for example as practiced for example in DE-A 102009027401 or in DE-A 102007004960.

Such thermal separation processes (for example all thermal separating processes described in WO 2011/000808 A2, DE-A 10336386, DE-A 19924532, DE-A 19924533, and DE-A 102007004960) are preferably performed according to the invention in apparatuses conforming to the recommendations of U.S. Pat. No. 6,441,228 B2 and U.S. Pat. No. 6,966,973 B2.

The heterogeneously catalyzed partial gas phase oxidation for producing acrylic acid may for example employ a reaction gas starting mixture comprising, based on the molar amount of the employed $C_3$-precursor compound present therein (for example propane, propylene, acrolein, propionic acid, propionaldehyde, propanol and/or glycerol, preferably propylene and acrolein), a total molar amount of $C_2$-compounds (for example ethane, ethylene, acetylene, acetaldehyde, acetic acid and/or ethanol) of ≥100 molar ppm, or ≥200 molar ppm, or ≥300 molar ppm, or ≥400 molar ppm, or ≥500 molar ppm, or ≥750 molar ppm, or ≥1000 molar ppm, or ≥2000 molar ppm, or ≥3000 molar ppm.

The aforementioned total molar amount of $C_2$-compounds in the reaction gas starting mixture of the heterogeneously catalyzed partial gas phase oxidation of the $C_3$-precursor compound to afford acrylic acid (on the same basis) is generally not more than 10 000 molar ppm.

In addition the reaction gas starting mixture used for the heterogeneously catalyzed partial gas phase oxidation for producing acrylic acid may comprise for example in the case of propylene or acrolein as the $C_3$-precursor compound (but also in the case of the other $C_3$-precursor compounds distinct from n-propane), based on the weight of the propylene/acrolein present (the $C_3$-precursor compound distinct from n-propane), 0.05% by weight of n-propane, or 0.2% by weight of n-propane, or ≥0.5% by weight of n-propane, or ≥1% by weight of n-propane, or ≥3% by weight of n-propane, or ≥5% by weight of n-propane, or ≥10% by weight of n-propane, or ≥20% by weight of n-propane. However, the reaction gas starting mixture of a heterogeneously catalyzed partial gas phase oxidation of propylene and/or acrolein (the $C_3$-precursor compound distinct from n-propane) to afford acrylic acid typically comprises not more than 80% by volume, often not more than 70% by volume and frequently not more than 60% by volume (but usually not less than 0.1% by volume) of n-propane.

The term "reaction gas starting mixture" is in all of the aforementioned cases to be understood as meaning the gas mixture supplied to the catalyst bed for the purpose of partial oxidation of the $C_3$-precursor compound present therein to afford acrylic acid. In addition to the $C_3$-precursor compound, unwanted impurities and molecular oxygen as an oxidizing agent, the reaction gas starting mixture generally also comprises inert diluent gases such as for example $N_2$, $CO_2$, $H_2O$, noble gas, molecular hydrogen, etc. Each of the inert diluent gases is normally constituted such that at least 95 mol % of the starting amount thereof remains unchanged in the course of the heterogeneously catalyzed partial oxidation.

The proportion of the $C_3$-precursor compound in the reaction gas starting mixture may be for example in the range from 4% to 20% by volume, or from 5% to 15% by volume, or from 6% to 12% by volume.

Based on the stoichiometry of the partial oxidation reaction of the $C_3$-precursor compound to afford acrylic acid, the reaction gas starting mixture normally comprises an excess of molecular oxygen to reoxidize the generally oxidic catalysts again.

In the case of a subsequent application of the process mode according to the invention this excess may be may be set particularly high since increasing oxygen excess is generally also accompanied by an increase in undesired glyoxal secondary component formation.

In the same way the maximum reaction temperature prevailing in the catalyst bed in the heterogeneously catalyzed partial gas phase oxidation of the $C_3$-precursor compound to afford acrylic acid may be set at a comparatively elevated level when the process according to the invention is employed subsequently to the partial oxidation. One reason for this is that increasing maximum temperature is generally also accompanied by an increase in undesired glyoxal secondary component formation. However, the use of elevated maximum temperatures generally permits the use of catalysts having a relatively low activity, thus raising the possibility of an extended catalyst service life. However, when using catalysts of relatively low activity, increasing conversion of the $C_3$-precursor compound is increasingly often also associated with undesired complete combustion thereof. Glyoxal may in some cases likewise be formed as an intermediate.

In the context of the process mode according to the invention it is similarly also possible to proceed more generously in the selection of the space velocity of $C_3$-precursor compound over the catalyst bed.

It has further been found that glyoxal by-product formation is favored by elevated steam contents in the reaction gas mixture. The process according to the invention is therefore of relevance not least when the reaction gas starting mixture used for the heterogeneously catalyzed partial gas phase oxidation of the $C_3$-precursor compound comprises ≥1% by weight, or ≥3% by weight, or ≥5% by weight, or ≥9% by weight, or ≥15% by weight, or ≥20% by weight of steam. However, the steam content of the reaction gas starting mixture is generally not more than 40% by weight, often not more than 30% by weight.

The process of heterogeneously catalyzed partial gas phase oxidation to produce acrylic acid may otherwise be performed in a manner known per se as described in the prior art.

When the $C_3$-precursor compound is for example propylene and/or acrolein the heterogeneously catalyzed partial gas phase oxidation may be performed for example as described in the specifications WO 2005/042459 A, WO 2005/047224 A and WO 2005/047226 A.

When the $C_3$-precursor compound is for example propane the heterogeneously catalyzed partial gas phase oxidation to produce acrylic acid may be performed for example as described in the specifications EP-A 608 838, DE-A 198 35 247, DE-A 102 45 585 and DE-A 102 46 119.

When the $C_3$-precursor compound is for example glycerol the heterogeneously catalyzed partial gas phase oxidation to produce acrylic acid may be performed for example as described in the specifications WO 2007/090991 A, WO 2006/114506 A, WO 2005/073160 A, WO 2006/114506 A, WO 2006/092272 A or WO 2005/073160 A.

It has also previously been proposed to obtain the propylene as $C_3$-precursor compound by a partial dehydrogenation and/or oxydehydrogenation of propane arranged upstream of the partial gas phase oxidation (for example WO 076370, WO 01/96271, EP-A 117146, WO 03/011804 and WO 01/96270).

The process according to the invention is especially also advantageously employable when the glyoxal present in the liquid phase P is to an extent of at least 20 mol %, or to an extent of at least 30 mol %, or to an extent of at least 50 mol %, or to an extent of at least 70 mol %, or to an extent of at least 90 mol %, or to an extent of at least 95 mol %, present in the liquid phase P in the form of monomeric glyoxal monohydrate and/or monomeric glyoxal dihydrate.

The process according to the invention is advantageous not least when the liquid phase P to be treated in accordance with the invention derives from a product gas mixture from a heterogeneously catalyzed partial gas phase oxidation of a $C_3$-precursor of acrylic acid which, based on the molar amount of acrylic acid present in the product gas mixture, comprises in the range from 25 to 1000 ppmw of glyoxal, in particular in the range from 50 to 500 ppmw of glyoxal (determination of the aforementioned glyoxal contents of the product gas mixture based on the molar amount of acrylic acid present may be achieved by cooling the latter, at least the acrylic acid present therein, the hemiacetals and/or acetals of glyoxal present therein and the monomeric glyoxal present therein to effect conversion into the condensed phase and analyzing the latter for its content of glyoxal and acrylic acid as soon as possible after production thereof as described for a liquid phase P in this document).

Liquid phases P to be treated in accordance with the invention are often also subjected to an azeotropic rectification to separate water present therein. Contemplated entraining agents suitable in this regard especially include heptane, dimethylcyclohexane, ethylcyclohexane, toluene, ethylbenzene, octane, chlorobenzene, xylene or mixtures thereof (for example 60% by weight of toluene and 40% by weight of heptane). However, methyl isobutyl ketone or isopropyl acetate may also be employed as alternative entraining agents. Otherwise, it is possible to proceed as described in the specifications EP-A 778255, EP-A 695736 and US 2004/0242826. Liquid phases P to be treated in accordance with the invention thus especially also include liquid phases P comprising at least one of the aforementioned entraining agents and water. In general the water content of such liquid phases P is at least 10% by weight and the content of azeotropic entraining agent is at least 1% by weight, often at least 2% by weight or at least 5% by weight.

The process according to the invention is also relevant not least when glyoxal and propionic acid present in a liquid phase P treated in accordance with the invention are separated therefrom by crystallization, wherein the glyoxal and the propionic acid are enriched in the remaining mother liquor and the acrylic acid is enriched in the crystallizate, and is recycled by the mother liquor into at least one of the process steps by means of which the liquid phase P treated in accordance with the invention has been obtained (produced) from the product gas mixture from the heterogeneously catalyzed partial gas phase oxidation of the $C_3$-precursor compound. The crystallizative separation process may be performed in corresponding fashion as described in the specifications DE-A 102008041573, DE-A 102008040799 and WO 2007/074044 A and also DE-A 102007029053.

Unless otherwise stated, ppm values are based on weight.

Unless otherwise stated, values reported in % are based on weight.

Unless otherwise stated, reported values are based on absolute pressure.

INVENTIVE AND COMPARATIVE EXAMPLES

Experimental Procedure

Preheat oil bath to 103° C.

100.0 g of acrylic acid (with appropriate additives) are filled into a 250 ml glass bottle (tared) (magnetic stirrer).

N2 is passed through the acrylic acid for 30 min (about 70 l/h).

After 30 min the N2 stream is only passed over the acrylic acid and reduced to 14-18 l/h.

Subsequently immerse the bottle in the preheated oil bath to the fill height (internal temperature 100° C.)

Stir at 100° C. for 2 h. Then lower the oil bath.

After achieving an internal temperature of 50° C. the remaining acrylic acid is decanted off. Amount of polymerized acrylic acid in % by weight based on initial weight.

EXAMPLES

The following examples with acrylic acid (purity >98% by weight) were carried out analogously with the above-described experimental procedure using different amounts of furfural and glyoxal. Each experiment was repeated 2-6 times and the average values obtained are reported.

|  |  | Furfural content [ppm] | Glyoxal [ppm] | Polymer [%] |
| --- | --- | --- | --- | --- |
| Example 1 | 200 ppm MeHQ | 0 | 0 | 2.9 |
| Example 2 | 200 ppm MeHQ | 500 | 0 | 4.4 |
| Example 3 | 200 ppm MeHQ | 0 | 50 | 35.7 |
| Example 4 | 200 ppm MeHQ | 50 | 50 | 11.1 |
| Example 5 | 200 ppm MeHQ | 100 | 50 | 7.3 |
| Example 6 | 200 ppm MeHQ | 200 | 50 | 8.2 |
| Example 7 | 200 ppm MeHQ | 500 | 50 | 6.5 |
| Example 8 | 200 ppm MeHQ | 0 | 100 | 68.1 |

-continued

| | | Furfural content [ppm] | Glyoxal [ppm] | Polymer [%] |
|---|---|---|---|---|
| Example 9 | 200 ppm MeHQ | 50 | 100 | 41.4 |
| Example 10 | 200 ppm MeHQ | 100 | 100 | 31.4 |
| Example 11 | 200 ppm MeHQ | 200 | 100 | 20.5 |
| Example 12 | 200 ppm MeHQ | 300 | 100 | 24.8 |
| Example 13 | 200 ppm MeHQ | 400 | 100 | 13.0 |
| Example 14 | 200 ppm MeHQ | 500 | 100 | 7.4 |
| Example 15 | 200 ppm MeHQ | 0 | 175 | 60.7 |
| Example 16 | 200 ppm MeHQ | 50 | 175 | 36.7 |
| Example 17 | 200 ppm MeHQ | 100 | 175 | 24.3 |
| Example 18 | 200 ppm MeHQ | 200 | 175 | 15.9 |
| Example 19 | 200 ppm MeHQ | 500 | 175 | 7.9 |
| Example 20 | 200 ppm MeHQ | 0 | 250 | 88.1 |
| Example 21 | 200 ppm MeHQ | 50 | 250 | 43.8 |
| Example 22 | 200 ppm MeHQ | 100 | 250 | 21.4 |
| Example 23 | 200 ppm MeHQ | 200 | 250 | 14.1 |
| Example 24 | 200 ppm MeHQ | 500 | 250 | 9.8 |
| Example 25 | 200 ppm MeHQ | 0 | 500 | 100.0 |
| Example 26 | 200 ppm MeHQ | 50 | 500 | 52.6 |
| Example 27 | 200 ppm MeHQ | 100 | 500 | 35.6 |
| Example 28 | 200 ppm MeHQ | 200 | 500 | 19.9 |
| Example 29 | 200 ppm MeHQ | 500 | 500 | 9.0 |
| Example 30 | 250 ppm PTZ | 250 | 94 | 41.0 |
| Example 31 | 250 ppm PTZ | 850 | 94 | 15.0 | ppm values are in ppmw
% values are in % by wt.

The invention claimed is:

1. A process for inhibiting the undesired free-radical polymerization of acrylic acid present in a liquid phase P, comprising providing a liquid phase P, wherein the acrylic acid content of P is at least 10% by weight, the liquid phase P comprises in the range from 25 to 1000 ppmw of glyoxal based on the weight of the acrylic acid present in P, admixing the liquid phase P with furfural in an amount that results in a furfural content in the range from 25 to 1000 ppmw based on the weight of the acrylic acid present in P, and inhibiting the free-radical polymerization of acrylic acid present in a liquid phase P.

2. The process according to claim 1, wherein the acrylic acid content of P is at least 30% by weight.

3. The process according to claim 1, wherein the acrylic acid content of P is at least 50% by weight.

4. The process according to claim 1, wherein the liquid phase P comprises in the range from 50 to 500 ppmw of glyoxal based on the weight of the acrylic acid present in P and the liquid phase P is admixed with furfural in an amount that results in a furfural content in the range from 50 to 500 ppmw based on the weight of the acrylic acid present in P.

5. The process according to claim 1, wherein the liquid phase P comprises in the range from 50 to 1000 ppmw of phenothiazine based on the weight of the acrylic acid present in P.

6. The process according to claim 1, wherein the liquid phase P comprises in the range from 50 to 1000 ppmw of methylhydroquinone based on the weight of the acrylic acid present in P.

7. The process according to claim 1, wherein said process is performed in the absence of oxygen.

8. The process according to claim 1, wherein the liquid phase P has a temperature in the range from 50° C. to 150° C.

9. The process according to claim 1, wherein said process is performed in a column for distillative recovery of acrylic acid.

10. The process according to claim 1, wherein the acrylic acid present in the liquid phase P is the product of a heterogeneously catalyzed partial oxidation of a $C_3$-precursor compound of acrylic acid, wherein the starting mixture comprising the $C_3$-precursor compound used for the partial oxidation comprises, based on the molar amount of the $C_3$-precursor compound present therein, a molar total amount of $C_2$-compounds in the range from 100 to 10 000 molar ppm.

11. The process according to claim 1, wherein the acrylic acid present in the liquid phase P is the product of a heterogeneously catalyzed partial oxidation of a $C_3$-precursor compound of acrylic acid, wherein the starting mixture comprising the $C_3$-precursor compound used for the partial oxidation comprises up to 80% by volume of n-propane.

12. The process according to claim 11, wherein the $C_3$-precursor compound is propylene, acrolein or n-propane.

* * * * *